United States Patent
Sparks

(10) Patent No.: US 6,514,523 B1
(45) Date of Patent: Feb. 4, 2003

(54) CARRIER PARTICLES FOR DRUG DELIVERY AND PROCESS FOR PREPARATION

(75) Inventor: Daniel L. Sparks, Aylmer (CA)

(73) Assignee: Ottawa Heart Institute Research Corporation, Ottawa (CA)

( * ) Notice: Subject to any disclaimer, the term of this patent is extended or adjusted under 35 U.S.C. 154(b) by 0 days.

(21) Appl. No.: 09/503,187

(22) Filed: Feb. 14, 2000

(51) Int. Cl.$^7$ .............................. A61K 9/27; A61K 9/20; B32B 5/16; B01J 13/02
(52) U.S. Cl. ..................... 424/450; 424/464; 264/4.1; 264/4.3; 264/4.6; 428/402.2
(58) Field of Search ................................ 424/450, 464; 264/4.1, 4.3, 4.6; 428/402.2; 436/829

(56) References Cited

U.S. PATENT DOCUMENTS

| | | | |
|---|---|---|---|
| 4,868,158 A | 9/1989 | Masquelier et al. | 514/21 |
| 5,128,318 A | 7/1992 | Levine et al. | 514/2 |
| 5,284,831 A | 2/1994 | Kahl et al. | 514/21 |
| 5,324,821 A | 6/1994 | Favre et al. | 530/359 |
| 5,576,016 A | 11/1996 | Amselem et al. | 424/450 |
| 5,652,339 A | 7/1997 | Lerch et al. | 530/359 |
| 5,795,587 A | 8/1998 | Gao et al. | 424/450 |
| 6,287,590 B1 | 9/2001 | Dasseux | |

FOREIGN PATENT DOCUMENTS

| | | |
|---|---|---|
| CH | 0663407 | 12/1994 |
| SE | 9904761 | 2/1999 |

OTHER PUBLICATIONS

Sylvie Braschi et al., "Apolipoprotein A–1 Charge And Conformation Regulate The Clearance Of Reconstituted High Density Lipoprotein In Vivo", (1999), Journal of Lipid Research, vol. 40, pp. 522–532.

Daniel L. Sparks et al., "Effects Of The Neutral Lipid Content Of High Density Lipoprotein On Apolipoprotein A–I Structure And Particle Stability", (1995), The Journal of Biological Chemistry, vol. 270, No. 45, pp. 26910–26917.

Jean Bergeron et al., "Characterization Of Human Apolipoprotein A–I Expressed in Escherichia Coli", (1997), Biochimica et Biophysica Acts, vol. 1344, pp. 139–152.

(List continued on next page.)

*Primary Examiner*—Thurman K. Page
*Assistant Examiner*—Amy E Pulliam

(57) ABSTRACT

This invention relates to a carrier particle having a diameter of from 5 to 20 nm which contains an HDL apolipoprotein, an amphipathic lipid such as a phospholipid, and a drug which is either a hydrophobic drug, amphipathic drug, or a cationic hydrophilic drug. The carrier particle is formed by a process in which the components are co-sonicated in a buffer. The apolipoprotein is preferably apo A-I or apo A-II. The carrier particle is particularly useful for increasing plasma circulation time of a hydrophobic drug relative to conventional hydrophobic drug carrier particles. Thus, drug efficacy is improved and toxicity of the drug to renal and reticuloendothelial tissues is reduced. A composition for drug delivery comprises the carrier particle suspended in a pharmaceutically acceptable medium, and is particularly suited to administration by parenteral infusion, systemic injection, transdermal patch, oral tablet or oral spray.

28 Claims, 3 Drawing Sheets

OTHER PUBLICATIONS

Kishor M. Wasan, "Modifications In Plasma Lipoprotein Concentration And Lipid Composition Regulate The Biological Activity Of Hydrophobic Drugs", (1996), Journal of Pharmacological and Toxicological Methods, vol. 36, pp. 1–11.

Kishor M. Wasan, "Influence Of Lipoproteins On Renal Cytotoxicity And Antifungal Activity Of Amphotericin B", Feb. 1994, Antimicrobial Agents and Chemotherapy, vol. 38, No. 2, pp. 223–227.

Versluis A.J. et al: "Stable Incorporation of a Lipophilic Daunorubic Prodrug into Apolipoprotein E–Exposing Liposomes Induces Uptake of Prodrug via Low–Density Lipoprotein Receptor In Vivo", Journal of Pharmacology and Experimental Therapeutics, Apr. 1999, vol. 289, No. 1, pp. 1–7.

Sparks D.L et al. "Effect of Apolipoprotein A–I Lipidation on the Formation and Function of Pre–$\beta$ and $\alpha$–Migrating LpA–I Particles". Biochemistry, Feb. 9, 1999, vol. 38, No. 6, pp. 1727–1729.

Wasan K.M. et al. "Influence of Lipoproteins on Renal Cytotoxicity and Antifungal Activity of Amphotericin B", Antimicrobial Agents and Chemotherapy, Feb. 1994, vol. 38, No. 2, pp. 223–227.

Wasan K.M. et al. "Roles of Liposome Compositions and Temperature in Distribution of Amphotericin B in Serum Lipoproteins", Antimicrobial Agents and Chemotherapy, Feb. 1993, vol. 37, No. 2, pp. 246–250.

CARRIER PARTICLES FOR DRUG DELIVERY AND PROCESS FOR PREPARATION

The invention relates to carrier particles for delivery of a drug and a process for preparation of carrier particles.

BACKGROUND OF THE INVENTION

Pharmaceutical delivery systems for hydrophobic drugs have conventionally involved formulating the drug with a carrier particle such as a liposome or an emulsion. Due in part to the large particle size and foreign shape of the particle, the body quickly recognizes these conventional particles as foreign and rapidly clears them from the plasma.

Rapid clearance of a drug reduces drug efficacy by limiting the availability of the drug to the target tissues. Drug toxicity in the clearance tissues, particularly renal toxicity, may result from the high drug concentration caused by this rapid clearance of hydrophobic drugs delivered by conventional carrier particles.

Liposomes consist of one or more concentric lipid bilayers separated by aqueous compartments, and having and aqueous core compartment. The concentric lipid bilayers are usually comprised of phospholipid bilayers. Liposomes can be used to deliver hydrophobic drugs by incorporation of the drug into the lipid bilayer, or may be used to deliver hydrophilic drugs by encapsulation of the drug in the aqueous compartments or core space. Depending on the number of concentric bilayers, and the quantity of substance encapsulated therein, liposomes may range in size from small unilamellar vesicles of about 50 nm in diameter to large multilamellar vesicles of up to 10 μm in diameter. Liposomes for delivery of a hydrophobic drug are disclosed, for example, in U.S. Pat. No. 5,795,587 (Gao et al.; Aug. 18, 1998).

Liposomes have the drawback that the amount of drug contained in each particle is limited. Unilamellar vesicles have a particularly low hydrophobic drug loading capacity, and are more effectively used for delivery of hydrophilic drugs in the particle core. Multilamellar liposomes are more suitable for hydrophobic drug incorporation, but due in part to the large particle size and foreign shape, the body quickly recognizes these conventional particles as foreign and rapidly clears them from the plasma.

Emulsions are heterogeneous systems of lipid particles dispersed in an hydrophilic or aqueous medium. Hydrophobic drugs may be incorporated into the lipophilic phase of the emulsion. Emulsion particles are often large in size and these particles frequently exceed 1 μm in diameter. To achieve smaller sized particles and to stabilize particles against coalescence, detergents or surfactants may be incorporated into an emulsions. Such stabilizers may disadvantageously act as hemolytic agents, thereby solubilizing membranes when injected into the body. Amphipathic lipids are those lipids which have both a hydrophobic and a hydrophilic moiety on the same molecule. An example of an amphipathic lipid is a phospholipid. Amphipathic lipids have been used to stabilize lipophilic drug emulsions.

Carrier particles referred to as "emulosomes", having features intermediate between liposomes and emulsions, are described in U.S. Pat. No. 5,576,016. Emulosomes have a lipid core containing, in combination with the hydrophobic drug of interest, a triglyceride, wax or ester which is in a solid or liquid crystalline phase at 25° C. The emulosome core is surrounded by an outer phospholipid monolayer or bilayer containing a surfactant. Emulosome particles are smaller than conventional emulsion particles, and range in size from 10 to 250 nm in diameter, having an average diameter from about 50 to 150 nm. However, such a heterogeneous particle size distribution may be disadvantageous, since metabolism of the particles may vary according to size.

Following intravenous administration of hydrophobic drugs in conventional liposome particles, transfer of the drug from the initial carrier to plasma lipoproteins occurs. Association of amphotericin B with native serum low-density lipoprotein (LDL) was shown to correlate with renal toxicity of the drug, possibly through LDL-receptor mediated drug uptake by kidney cells (J. Pharm. Tox. Meth. 1996;36:1–11). Additionally, it has been shown that the more rapidly or completely amphotericin B is transferred from a liposomal particle to native serum high-density lipoprotein (HDL) in vivo, the less renal toxicity it displays (Antimicrob. Agents Chemother. 1994;38:223–227). Thus, HDL-associated amphotericin B exhibits less renal toxicity than LDL-associated amphotericin B.

U.S. Pat. No. 4,868,158 (Masquelier et al.; Sep. 19, 1989) teaches a method for the production of a complex containing reconstituted LDL which carries a lipophilic drug. Lyophilized LDL was mixed with the drug, a solvent, and a protective agent to stabilize the resulting complex, for example, a sugar alcohol, or a mono-, di- or poly-saccharide. The solvent was removed and the LDL-drug complex was then reconstituted. This LDL-drug complex is intended in part to target the drug to cells having high levels of LDL receptors.

U.S. Pat. No. 5,324,821 (Favre et al.; Jun. 28, 1994) discloses a method of incorporating a lipophilic drug into a lipoprotein complex, preferably containing LDL. The method involves preparing an emulsion, adding the lipophilic drug, the lipoprotein and a lipid transfer protein, and incubating the mixture. Those lipoproteins complexed with the drug may then be isolated from the incubation mixture and used for pharmaceutical purposes.

Methods for preparing reconstituted HDL particles are known. For example, U.S. Pat. No. 5,652,339 (Lerch et al.; Jul. 29, 1997) discloses a method of producing reconstituted HDL particles from apolipoprotein A-I and phosphatidyl choline. However, this document does not teach the use of reconstituted HDL for hydrophobic drug delivery.

U.S. Pat. No. 5,128,318 (Levine et al.; Jul. 7, 1992) describes a method for reconstituting HDL-like particles using a detergent dialysis emulsification technique. Sodium cholate, a bile acid, is used as a detergent to effect emulsification. The resulting HDL-containing particles are disc-shaped, unlike native HDL. The particles are intended for use in removing excess lipid-soluble material, such as endotoxin, from a subject. In use in vivo, lipid-soluble material moves into the centre of the disc-shaped carrier. This document does not describe the preparation of a drug carrier complex or any methodology for associating a drug with the particle.

The present invention provides carrier particles which are small in size and not easily recognized as foreign by the body for drug delivery of hydrophobic, amphipathic, or cationic lipophilic drugs. The present invention further provides a process for preparing carrier particles comprising drugs. It is an object of the invention to circumvent drawbacks in hydrophobic drug delivery described in the prior art.

The above object is met by the combinations of features of the main claims, the sub-claims disclose further advantageous embodiments of the invention.

SUMMARY OF THE INVENTION

The invention relates to carrier particles for delivery of a drug and a process for preparation of carrier particles.

According to the invention, there is provided carrier particles for a drug and a method for the preparation of a carrier particles and a drug. The carrier particle comprises at least one HDL apolipoprotein, preferably apolipoprotein A-I (apo A-I) or apolipoprotein A-II (apo A-II), at least one amphipathic lipid, and at least one drug selected from the group consisting of hydrophobic drug, an amphipathic drug, and a cationic hydrophilic drug. The carrier particle has a diameter of from about 5 nm to about 20 nm.

The invention additionally provides a composition for delivery of a hydrophobic, amphipathic or cationic hydrophilic drug which comprises carrier particles, as described above, in combination with a pharmaceutically acceptable medium in which the carrier particles are dissolved or suspended. The carrier particle may comprise a lipid-soluble component, selected from the group consisting of:

i) a fatty acid having from 8 to 24 carbons, said fatty acid either saturated or containing one or more unsaturated bonds;

ii) an ester of said fatty acid;

iii) mono-, di-, and tri-glycerides of said fatty acid;

iv) cholesterol, or an ester thereof;

v) an antioxidant;

vi) a steroid hormone;

vii) a small hydrophobic peptide;

viii) vitamin A, D, E, or K; and ix) β-carotene.

According to the invention, a method is provided for delivery of a hydrophobic, amphipathic or cationic hydrophilic drug to a mammalian subject comprising administering to the subject an effective amount of the above-described carrier particle or composition.

Thus, in one aspect, the invention provides a process for preparing a synthetic HDL spherical particle comprising at least one HDL apolipoprotein, at least one amphipathic lipid, and at least one hydrophobic active agent, said process consisting essentially of the steps of: (a) admixing at least one amphipathic lipid with at least one hydrophobic active agent in a solvent, said at least one hydrophobic active agent being selected from the group consisting of a hydrophobic drug, an amphipathic drug, and a lipid-soluble component; (b) removing said solvent to produce a dried mixture; (c) hydrating said dried mixture in an aqueous buffer to produce an aqueous mixture, said aqueous buffer being essentially free of detergent; (d) adding at least one HDL apolipoprotein to said aqueous mixture; and (e) vigorously mixing by sonication, trituration, or homogenization said HDL apolipoprotein and said aqueous mixture to form said synthetic HDL spherical particle.

In a further aspect, the invention provides a synthetic HDL spherical particle made by the process described herein, said synthetic HDL spherical particle comprising: at least one HDL apolipoprotein, at least one amphipathic lipid, and at least one hydrophobic active agent, said hydrophobic active agent being selected from the group consisting of a hydrophobic drug, an amphipathic drug, and a lipid-soluble component, and said synthetic HDL spherical particle being generally spherical and having a diameter of from about 5 nm to about 20 nm.

In a further aspect, the invention provides a composition comprising: (a) a spherical carrier particle comprising at least one HDL apolipoprotein and at least one amphipathic lipid; and (b) a hydrophobic active agent entirely disposed within the spherical carrier particle of (a) to form a synthetic HDL spherical particle having a diameter of from about 5 nm to 20 nm, said hydrophobic active agent being selected from the group consisting of a hydrophobic drug, an amphipathic drug, and a lipid-soluble component.

Further, according to the invention, there is provided a process for preparing carrier particles for a hydrophobic, amphipathic, or cationic hydrophilic drug comprising the steps of: (a) mixing an amphipathic lipid with at least one drug in a solvent; (b) removing the solvent to produce a dried mixture; (c) hydrating the dried mixture in an aqueous buffer to produce an aqueous mixture; (d) adding at least one HDL apolipoprotein to the aqueous mixture; and (e) vigorously mixing the apolipoprotein with the aqueous mixture to form carrier particles. The particles formed according to this method contain the drug and have a diameter of from about 5 nm to about 20 nm.

Without being bound by theory, the apolipoprotein component of the particle helps to disguise the particle so that the body does not immediately recognize it as foreign, but may allow the body to perceive it as native HDL. The small size and the approximately spherical shape allow the particle to exhibit similar physicochemical properties to native HDL. Because the carrier particles are not recognized as foreign, the systemic circulation of the drug increases, thus increasing the likelihood of drug delivery to the target tissues. Additionally, the clearance rate of the drug decreases, thereby reducing the likelihood of toxic effects of the drug on clearance tissues since accumulation of the drug in clearance tissues is reduced, especially for hydrophobic drugs. Furthermore, specific organs may be targeted by using carrier particles as described herein, due to target cells comprising high levels of specific receptors, for example but not limited to apoA-I receptors.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENTS

Figure 1:
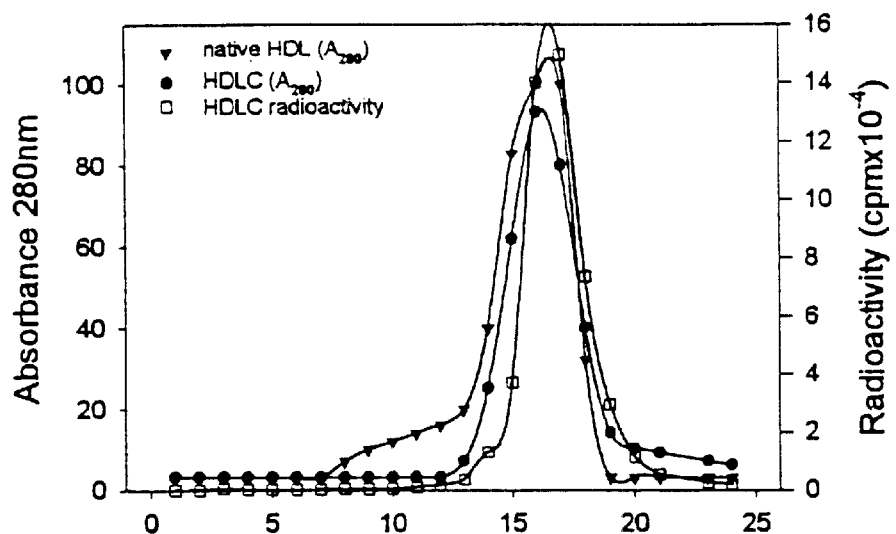
FIG. 1 is a graphical representation displaying the elution profile of human HDL apolipoprotein ((▼) native HDL) in relation to carrier particles comprising cyclosporin A ((●) HDLC($A_{280}$)) and carrier particles comprising $^{14}$C-labelled cyclosporin ((□) HDLC radioactivity) following Superose 6 size exclusion chromatography.

The present invention relates to carrier particles for delivery of a hydrophobic, amphipathic, or cationic hydrophilic drug, and to a process for forming the carrier particles.

The following description is of a preferred embodiment by way of example only and without limitation to the combination of features necessary for carrying the invention into effect.

With reference to FIGS. 1 to 4, the invention will now be described in further detail. The carrier particle comprises an HDL apolipoprotein, an amphipathic lipid, and a hydrophobic, amphipathic or cationic hydrophilic drug. Carrier particles are formed by mixing an amphipathic lipid and the drug in a solvent. The solvent is then removed and the dried lipid mixture is hydrated with an aqueous buffer. HDL apolipoprotein is then added and the composition is mixed vigorously to effect the formation of the carrier particles. The carrier particles so formed are spherical and have a diameter of from about 5 nm to about 20 nm. If desired, but not absolutely necessary, the carrier particles may be subjected to size exclusion chromatography to yield a more homogeneous preparation.

HDL apolipoproteins include, for example apolipoprotein A-I, (apo A-I), apolipoprotein A-II (apo A-II), apolipoprotein A4 (apo A4), apolipoprotein Cs (apo Cs), and apolipoprotein E (apo E). Preferably, the carrier particles are composed of Apo A-I or Apo A-II, however the use of other lipoproteins including apolipoprotein A4, apolipoprotein Cs or apolipoprotein E may be used alone or in combination to formulate carrier particle mixtures for delivery of drugs. Heterogeneous mixtures of apolipoproteins may affect the specific targeting and delivery of specific drugs. The use of apolipoprotein A4 is less preferable as this lipoprotein tends to be less stable than other isoforms and has the propensity to aggregate in solution. However, the use of Apo A4 may be used for certain applications as desired. Preferably, the particle carrier comprises apo A-I, apo A-II, or a combination thereof. When the drug particle carriers are to be administered to a human, preferably the particle carriers comprise apo A-I.

The amount of apolipoprotein in the carrier particle is from about 25% to about 50% (dry weight/weight) HDL apolipoprotein, for example but not limited to about 38% (dry weight/weight).

By the term "amphipathic lipid" is meant any lipid molecule which has both a hydrophobic and a hydrophilic moiety. For example, but not wishing to limit the scope of the invention, amphipathic lipids may include phospholipids or glycolipids. Examples of phospholipids which may be used in the carrier particle include but are not limited to phosphatidylcholine, phosphatidylinositol, phosphatidylserine, phosphatidylethanolamine, and combinations thereof.

The particle comprises from about 20% to about 50% (dry weight/weight) amphipathic lipid and is preferably about 30% (dry weight/weight).

By the term "drug" as used herein, is meant any molecular entity, including salts and derivatives, which may be administered to an individual for the purpose of providing a therapeutic, diagnostic or metabolic effect. Drugs for use with the invention comprises those drugs which are poorly soluble in an aqueous medium, as well as cationic hydrophilic drugs or amphipathic drugs. Hydrophobic drugs which may beneficially be incorporated into the drug delivery formulation according to the invention include for example but are not limited to, ametantrone, amphotericin B, annamycin, cyclosporin, daunorubicin, diazepam, doxorubicin, elliptinium, etoposide, ketoconazole, methotrexate, miconazole, mitoxantrone, nystatin, phenytoin, vincristine, other compounds may include, but are not limited to cytokines, or steroidal hormones, for example estragenic (e.g. estradiol), androgenic (e.g. testosterone) hormones, or other hormones that comprise a sterol backbone. Mixtures of more than one drug can also be incorporated into one composition for the purpose of co-administration. Drug formulations comprising cationic hydrophilic, or amphipathic drugs which complex with HDL-apolipoprotein are also contemplated by the present invention.

The capacity of the carrier particle to for a drug is up to about 20% (dry weight/weight). The drug carrying efficiency, and the upper limit of incorporation of a drug with a carrier particle depends on specific characteristics of the drug used. Without wishing to be limiting these characteristics include the size, the hydrophobicity of the drug, and the efficacy of the drug to be administered.

The carrier particles of the present invention are useful for the delivery of an amphipathic, or a cationic or a hydrophilic drug within a subject in need thereof. Without wishing to be bound by theory, the amphipathic, cationic or hydrophilic drug may associate with an HDL carrier particle via electrostatic, hydrophobic, covalent interactions, hydrogen bonding, or a combination thereof, or through Van der Waals forces, or a combination of any of the above associations. However it is to be understood that the carrier particles may associate with the amphipathic, cationic or hydrophobic drug in a reversible manner, with the equilibrium constant for this association towards the associated form.

Preferably, the carrier particle comprises approximately 1–20% by dry weight drug, approximately 20–50% by dry weight amphipathic lipid and approximately 25–50% by dry weight apolipoprotein. Also contemplated by the invention are carrier particles comprising approximately 20% by dry weight drug, with the amounts of amphipathic lipid and apolipoprotein adjusted to effectively solubilize the drug for efficient drug dosage, absorption and bioavailability.

Further contemplated by the present invention is apolipoprotein A-I and apolipoprotein A-II isolated from a variety of organisms, for example but not limited to bacteria (e.g. Begeron et al 1997, BBA 1355: 139–152), insects, or other expression systems for the production of recombinant protein, or non-human animals for example, but not to be considered limiting rabbit (Braschi et al., J Lipid Res (1999) 40(3):522–32; herein incorporated by reference), and formulated as carrier particles to be administered to a human subject. Preferably, the non-human HDL exhibits minimal immunological reaction within the subject. The non-human HDL apolipoprotein may also be prepared according to the present invention and administered concurrently or following administration of one or more immunosuppressive agents. Further contemplated are genetically modified HDL apolipoprotein isozymes which can be formulated as carrier particles with drugs as described herein. Also contemplated by the present invention is the formulation of carrier particles for drug delivery in domestic animals and livestock.

Other lipid-soluble components may be incorporated into the carrier particle as desired. Dilution of the drug to be delivered with other components may be required to achieve the optimum drug concentration within the carrier particle. Additional lipid-soluble components which may be incorporated into the carrier particle include but are not limited to fatty acids having from 8 to 24 carbons, which may be saturated or have one or more unsaturated bond, for example, palmitic, stearic, oleic, linolenic, and linoleic acids. Esters, mono-, di- or triglycerides of these fatty acids, cholesterol or esters thereof, steroid hormones, small hydrophobic peptides, antioxidants or vitamins such as vitamins A, D, E, K, or β-carotene may also be included.

A particle formulated according to the invention may contain about 38% (dry weight/weight) of apo A-I, about 47% (dry wt/wt) phospholipid, and about 15% (dry wt/wt) of the drug of interest.

The particles formed according to the invention range in average diameter from about 5 nm to about 20 nm in diameter depending upon the constituent HDL. For example, The carrier particles comprising apo A-I exhibit a diameter of from about 5 nm to about 15 nm, with the preferred average diameter of particles of about 7.5 nm. Carrier particles essentially comprising apo A-II exhibit a diameter of from about 10 nm to about 20 nm Carrier particles comprising a mixture of apo A-I and apo A-II will have a diameter from about 5 nm to about 20 nm. Carrier particles of these sizes are comparable to native HDL particles, which range in size from about 5 nm to about 12 nm in diameter. Without wishing to be bound by theory, the carrier particles according to the invention are advantageously sized and shaped to be recognized as non-foreign, as compared to conventional liposomal or emulsion particles which may range from 50 nm to more than 1 μm in diameter. Moreover, the small diameter of the particles ensures that they pass easily through the vasculature, a current drawback of formulations comprising relatively large particle sizes.

As illustrated in FIG. 1, native HDL particles obtained according to Comparative Example 1 are similar in size to HDL particles formed with cyclosporin A according to the invention as described in Example 1. FIG. 1 indicates that the greatest concentration of both native HDL particles and HDL particles comprising cyclosporin A elute at the same volume during size exclusion chromatography. Particles eluting in this region exhibit an average diameter of about 10 nm. Earlier eluting fractions, such as fractions 10 to 15 of FIG. 1 contain particles having a diameter of about 7.5 nm. The small size and the generally spherical shaped particles allow for sterilization of an aqueous composition containing the particles by passing the composition through a sterilization filter membrane after preparation and prior to use. Carrier particles are treated to remove endotoxin prior to use in humans.

According to one embodiment of the invention, the carrier particles are formed by mixing of an amphipathic lipid and a drug of interest in a suitable organic solvent. Chloroform, methylene chloride or methanol are suitable organic solvents, but any highly volatile solvent capable of solubilizing the amphipathic lipid and the drug to be formulated may also be used, providing the solvent has no adverse effects on either the drug or the amphipathic lipid. For example, but not to be considered limiting, the amphipathic lipid and the drug may be individually solubilized in chloroform and subsequently dried in a sonication vessel, to avoid the need for premixing. If other lipid-soluble components are to be added to the carrier particle, these may be added to and dissolved in the lipid/solvent mixture.

Solvent is removed according to any conventional solvent-removal technique. Solvent evaporation may be effected under reduced pressure for instance, with or without the presence of drying agents such as phosphorus pentoxide or alternatively the solvent may be evaporated under the steady stream nitrogen, argon or the like. Following solvent removal, the dried lipid mixture is hydrated using an appropriate aqueous buffer, for example but not to be considered limiting, phosphate buffered saline (PBS), or any other buffer which is acceptable for use in humans.

Following addition of the aqueous buffer, apolipoprotein is added to the mixture and the resulting mixture, is vigorously mixed using an appropriate method, for example by sonication, trituration, or homogenization, to achieve particles of adequately small size. Trituration is known in the art as meaning to pulverize and comminute thoroughly by rubbing or grinding (e.g. see *Webster's Ninth New Collegiate Dictionary,* Thomas Allen & Son Limited, Markham, Ontario; © 1989). The particles formed as a result may range in average diameter from about 5 nm to about 10 nm, and are spherical in shape. Size exclusion chromatography can be incorporated to purify particles of a preferred size.

The carrier particles containing a hydrophobic drug may be administered in a composition comprising the carrier particles and a pharmaceutically acceptable medium in which the carrier particles are suspended. The preferred route of administration of the composition is systemic, for example, by injection or parenteral infusion. However, the composition may be delivered by other routes, such as topical, interocular, oral, intranasal or rectal administration. Recently, the intestinal receptor, cubulin has been shown to exhibit high affinity binding for apoA-I (Kozyraki R. et al. 1999, Nat Med., 5:656–661), thereby providing a mechanism for oral uptake of carrier particles comprising apoA-I.

In an alternate embodiment, the carrier particles comprising drugs prepared according to Example 1, may be lyophilized and packaged into tablets or capsules with or without pharmaceutically acceptable filler materials for oral delivery. Similarly, carrier particles comprising drugs prepared according to the present invention, for example but not limited to those prepared according to Example 1, may be administered through the skin using a patch as is known in the art, or to the lungs via aspiration or spray.

The carrier particles may be suspended in a liquid medium consisting of the aqueous buffer in which the carrier particles were formed to form a composition according to an embodiment of the invention. The carrier particles of a desired size may be isolated from the buffer in which they were formed by size exclusion chromatography, and re-suspended in any pharmaceutically acceptable medium. The composition may be filtered, diluted, or sterilized, as desired. The particles may be included in a composition comprising a semi-solid medium, for example a cream, if the composition is to be administered topically, or rectally.

Drugs delivered with the carrier particles according to the invention can be targeted to specific locations in the body. These locations may include individual cells or tissues in specific organs. For example, carrier particles comprising drugs may be effectively targeted to cells and tissues which contain high levels of apo A-I receptors, for example but not limited to, cubulin (Kozyraki R. et al. 1999, Nat Med., 5:656–661) or the scavenger receptor, SR-B1 (Kozarsky K. F. et al. 1997, Nature, 387:414–417). Similarly, other formulations comprising additional components which target carrier particles comprising drugs to other target tissues may be incorporated into the particle carriers. Differently charged particles are taken up at different rates by different tissues.

Figure 2:
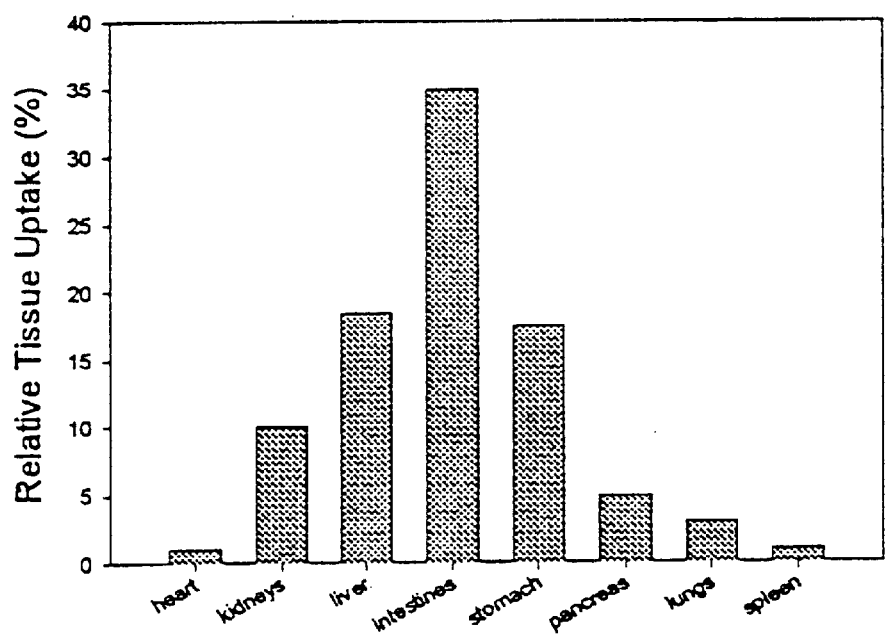
FIG. 2 illustrates the relative uptake of $^{14}$C-cyclosporin A in various rabbit tissues following intravenous injection of carrier particles comprising $^{14}$C-cyclosporin A prepared according to Example 1, at six hours post injection.

FIG. 2 illustrates tissue uptake of carrier particles comprising $^{14}$C-labelled cyclosporin formed according to the invention. These results indicate that tissues such as the liver, intestines, and stomach may be effectively targeted using the composition of the present invention. However, due to the longer circulation time (slower plasma clearance rate) as compared to conventional drug carrier particles, it is less likely that toxicity will result from rapid accumulation of the drug of interest in these tissues. Plasma circulation time and tissue uptake may be controlled by changing the electrostatic properties of the particles, which in turn depends on lipid content. Without wishing to be bound by theory, the conformation and charge of apoA-I within the particle of the instant invention regulate the clearance of HDL from plasma in rabbits, as shown for example in Braschi et al. *J. Lipid. Res.* (1999) March;40(3):522–32.

It is known that the lipid content of a reconstituted HDL particle affects the conformation of the apoA-I contained therein. The neutral lipid content and the cholesterol ester-:triglyceride ratio of a reconstituted HDL particle can effect the stability of the particle. Because the in vitro metabolism of reconstituted HDL is influenced by apoA-I charge and conformation (*J. Biol. Chem.* 1996; 271:25145–25151), metabolism of the carrier particles of the present invention are also effected by lipid composition. Plasma half-life of the carrier particles and uptake of the drug by particular tissues can be controlled by changing the electrostatic properties of the carrier particle. The lipid content of a particle in its entirety affects the stability and conformation of apo A-I, as demonstrated for example in Sparks et al., *J. Biol. Chem.* (1992) 267:25839–25847; Sparks et al., *J. Biol. Chem.* (1993) 268:23250–23257; Davidson et al., *J. Biol. Chem.* (1994) 269:8959–8965; Sparks et al., *J. Biol. Chem.* (1995) 270:26910–26917; Sparks et al. *Biochim. Biophys. Acta.* (1998) 1390:160–172; Braschi et al., *J. Lipid Res.* (1999) 40:522–532; and Sparks et al. *Biochemistry* (1999) 38:1727–1735.

The above description is not intended to limit the claimed invention in any manner, furthermore, the discussed combination of features might not be absolutely necessary for the inventive solution.

The present invention will now be described in more detail according to specific examples. These examples are for illustrative purposes only and should not be used to limit the invention in any way.

EXAMPLES

Examples are provided herein which describe particular embodiments of the invention. The examples are not to be construed as limiting. The invention encompasses such modifications to the exemplified embodiments as would occur to one skilled in the art.

Example 1
Preparation of Carrier Particles Comprising Cyclosporin

The carrier particles may comprise, but are not limited to, hydrophobic drugs such as cyclosporin for systemic delivery. The formation of carrier particles and a composition of carrier particles comprising cyclosporin particles is described.

Carrier particles comprising cyclosporin are prepared from 1-palmitoyl 2-oleoyl phosphatidylcholine (POPC) as the amphipathic lipid, cyclosporin A as the drug and substantially pure human HDL apolipoprotein A-I as the apolipoprotein, in the dry weight percent ratio of about 30:50:20 (apo-AI:POPC:cyclosporin). The purified amphipathic lipid and cyclosporin are suspended in chloroform and dried to completion under nitrogen. To 3.2 mg of the dried lipid mixture, 1.0 mL of an aqueous buffer containing phosphate buffered saline (50 mM phosphate buffer (pH 7.2), 150 mM NaCl) is added. The lipid-buffer solution is sonicated for 10 minutes using a Branson 450 sonicator equipped with a ⅛" tapered microtip probe. All sonications are performed under nitrogen in 12×75 mm test-tubes at 37° C. To this solution, 2.0 mg of apo A-I (in a 1.4 mg/mL solution) is added. The mixture is then sonicated in a bath sonifer for 10 minutes at 37° C. and then probe sonicated for 5×1 minute, with 1 minute cooling periods interspersed between probe sonications (see Sparks D. L. et al. J Biol. Chem. 270: 26910–26917, 1995). This mixture is then filtered through a 0.22 µm syringe tip filter. Carrier particles containing apo A-I and cyclosporin are re-isolated by size exclusion chromatography. Briefly, the particles are eluted in the same aqueous buffer as described above. Prior to injection the particles are diluted 50% with sterile saline such that the resulting formulation for injection comprises 25 mM phosphate in isotonic saline.

Comparative Example 1
Isolation of Native HDL Particles

Native HDL were isolated from fasting human plasma by sequential ultracentrifugation according to the method of Havel (J. Clinical Invest (1955) 34, 1345–1353).

Comparative Example 2
Preparation of $^{125}$I-Labelled Particles without Drug

A comparative particle not containing a drug is prepared from 1-palmitoyl 2-oleoyl phosphatidylcholine (POPC) as the amphipathic lipid and pure $^{125}$I-labelled (labelled using Iodo-Beads (Pierce) as disclosed in Braschi S. et al.,1999, J Lipid Res. 40: 522–532) human HDL apolipoprotein A-I in a molar ratio of 120:2. The amphipathic lipid is suspended in chloroform and dried to completion under nitrogen. To 3.2 mg of the dried lipid mixture, 1.0 mL of an aqueous buffer containing phosphate buffered saline (50 mM phosphate buffer (pH 7.2), 150 mM NaCl) is added. The lipid-buffer solution is sonicated, and subsequently processed as described for Preparation of Carrier Particles Comprising Cyclosporin in Example 1.

Comparative Example 3
Preparation of Liposomes Containing Cyclosporin

To 4.8 mg of POPC, 1.9 mg of cyclosporin A (comprising a small amount of $^{14}$C-labeled cyclosporin A) is added and both components are dissolved in chloroform and dried to completion under nitrogen. To 3.2 mg of the dried lipid-drug mixture, 1.0 mL phosphate buffered saline (50 mM phosphate buffer (pH 7.2), 150 mM NaCl) is added. The solution is sonicated and processed as described for Preparation of Carrier Particles Comprising Cyclosporin in Example 1.

Experiment 1
Particle Size Determination

Carrier particles prepared according to Example 1 and containing either cyclosporin A or $^{14}$C-cyclosporin A were compared to particles prepared according to Comparative Example 1. FIG. 1 shows Superose™ 6 size exclusion chromatograms of these particles. The size profiles of native HDL particles and carrier particles comprising cyclosporin formed according to the invention are similar. This data suggests that a high percentage of the cyclosporin was incorporated into the particles formed according to the process outlined in Example 1. Fraction numbers 10 to 15 correspond, to particles having an average diameter of about 7.5 nm.

Experiment 2

Tissue Uptake

Carrier particles prepared according to Example 1 and containing $^{14}$C-cyclosporin A were prepared and injected intravascularly into a New Zealand White rabbit. FIG. 2 illustrates relative tissue uptake of the drug in the animal after a period of 6 hours. While liposomal cyclosporin has previously been shown to be taken up by the kidneys and the reticuloendothelial system (primarily liver and spleen), cyclosporin delivered via particle carriers formed according to the invention and as outlined in Comparative Example 3, accumulate in gastrointestinal tissues, particularly the intestine. Plasma half-life of the carrier particles and uptake of the drug by particular tissues can be controlled by changing the electrostatic properties of the carrier particle.

Experiment 3

Plasma Clearance Rates

Intravenous clearance rates from rabbit plasma were determined for various carrier particles prepared according to the invention as outlined in Example 1. The carrier particles tested were as follows:

(a) carrier particles comprising native HDL particles prepared according to Comparative Example 1. These HDL carrier particles were $^{125}$I-labelled as previously described (Braschi S. et al. 1999, J Lipid Res. 40: 522–532).

(b) $^{125}$I-labelled apo A-I carrier particles prepared according to Comparative Example 2;

(c) apo A-I carrier particles were prepared, according to the invention, as outlined in Example 1, with $^{14}$C-labelled cyclosporin; and (d) a phospholipid-containing liposome carrier particle containing $^{14}$C-labelled cyclosporin, prepared according to Comparative Example 3.

Figure 3:
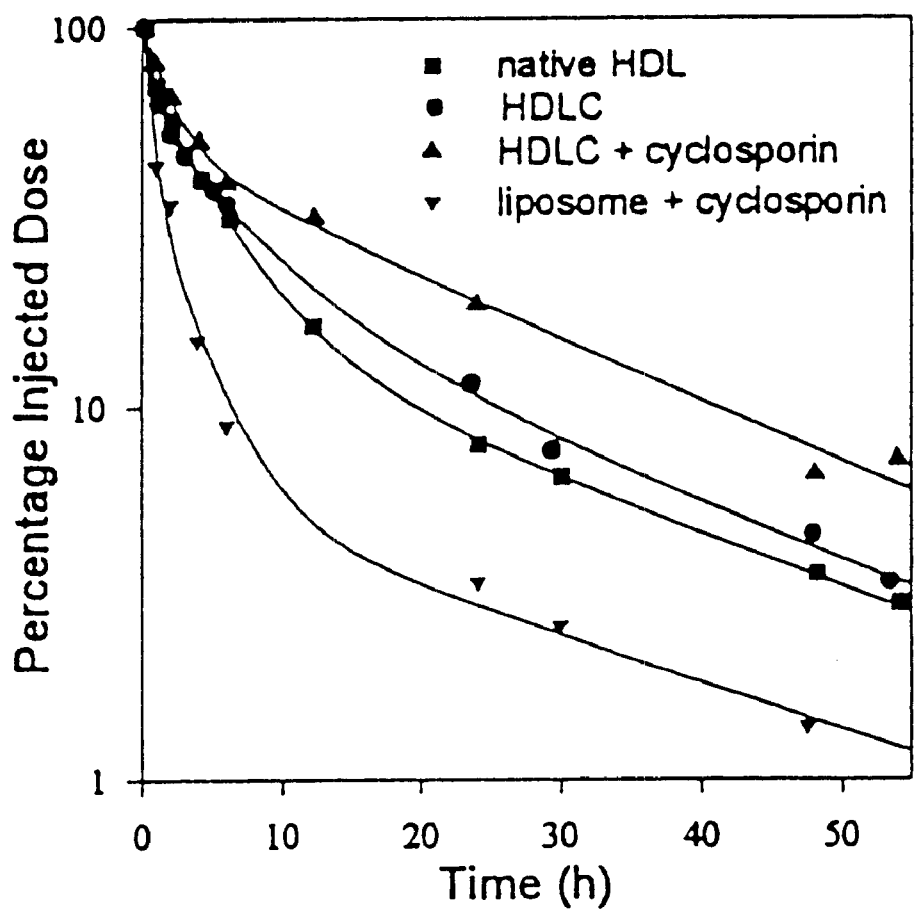
FIG. 3 is a graphic representation of clearance rates of $^{125}$I-labelled native HDL apolipoprotein particles ((■) native HDL); $^{125}$I-labelled HDL apolipoprotein particles (●) prepared according to example 1 except that the drug was omitted (HDLC); HDL apolipoprotein carrier particles comprising $^{14}$C-cyclosporin ((▲) HDLC+cyclosporin); and a phospholipid-containing liposome containing $^{14}$C-cyclosporin (▼). Clearance rates were determined by the relative amount of radioactive species in rabbit plasma over the course of 54 hours following intravascular injection

The results of clearance experiments shown in FIG. 3 indicate that the liposomal carrier particle results in the most rapid clearance of cyclosporin from the plasma. At six hours post-injection, less than 10% of the injected cyclosporin dose delivered in the liposomal carrier particle (d) remained in circulation. At forty-seven hours post-injection, about 1% of the injected dose remained in circulation. However, at six hours post-injection, about 40% of the cyclosporin delivered in carrier particles (c), prepared according to the invention as outlined in Example 1, remained in circulation. At fifty four hours post-injection about 7% of the injected dose remained in circulation.

These results indicate that a hydrophobic drug delivered via carrier particles is cleared more slowly from plasma circulation than if delivered using conventional liposome technology.

Experiment 4

Figure 4:
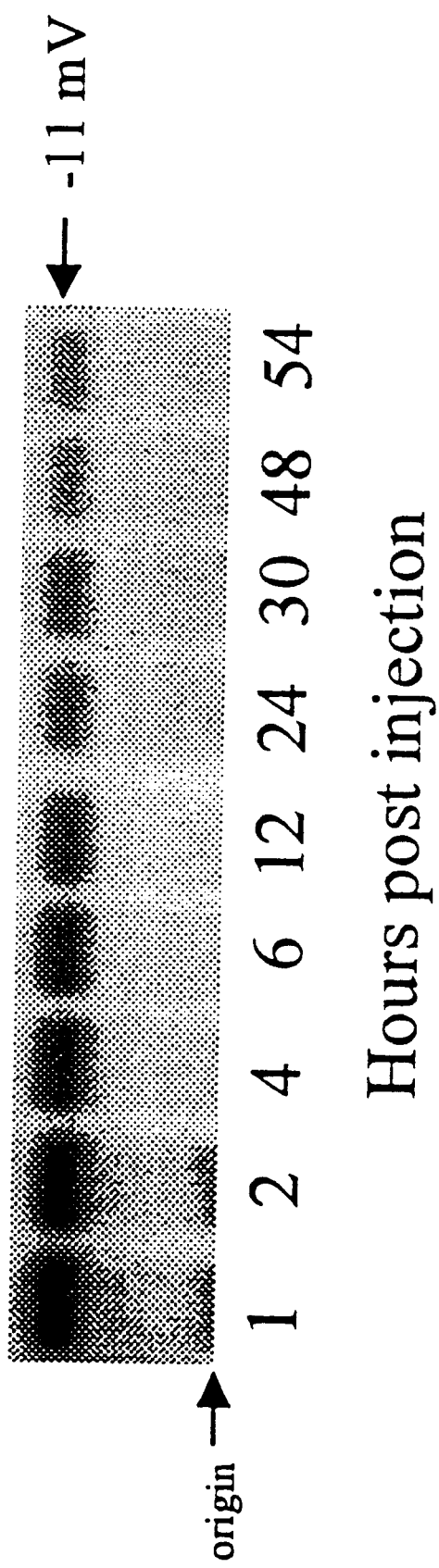
FIG. 4 is an autoradiograph depicting the stability of carrier particles comprising cyclosporin A in rabbit plasma as a function of time following intravenous injection. Samples were subject to agarose electrophoresis using 0.5% agarose gels.

FIG. 4 illustrates the stability of carrier particles comprising cyclosporin in rabbit plasma as a function of time. Carrier particles comprising cyclosporin were prepared according to Example 1, using $^{125}$I-labelled HDL apo A-I and cyclosporin. These carrier particles were administered via intravenous injection to rabbits and samples were obtained over time for analysis using agarose (0.5%) gel electrophoresis. Significant amounts of the $^{125}$I-labelled carrier particles remain in circulation even between 12 and 54 hours post-injection. The constant electrophoretic mobility over time of these particles shows that the particle exhibits a single band of constant charge, indicating no dissolution or degradation of the particle over time.

All publications cited herein are incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A process for preparing a synthetic HDL spherical particle comprising at least one HDL apolipoprotein, at least one amphipathic lipid, and at least one hydrophobic active agent, said process consisting essentially of the steps of:

(a) admixing at least one amphipathic lipid with at least one hydrophobic active agent in a solvent, said at least one hydrophobic active agent being selected from the group consisting of a hydrophobic drug, an amphipathic drug, and a lipid-soluble component;

(b) removing said solvent to produce a dried mixture;

(c) hydrating said dried mixture in an aqueous buffer to produce an aqueous mixture, said aqueous buffer being essentially free of detergent;

(d) adding at least one HDL apolipoprotein to said aqueous mixture; and (e) vigorously mixing by sonication, trituration, or homogenization said HDL apolipoprotein and said aqueous mixture to form said synthetic HDL spherical particle.

2. The process according to claim 1, wherein said step of mixing, step (e), consists essentially of sonication.

3. A process for preparing a synthetic HDL spherical particle comprising at least one HDL apolipoprotein, at least one amphipathic lipid, and at least one hydrophobic active agent, said process consisting essentially of the steps of:

(a) admixing at least one amphipathic lipid with at least one hydrophobic active agent in a solvent, said at least one hydrophobic active agent being selected from the group consisting of a hydrophobic drug, an amphipathic drug, and a lipid-soluble component;

(b) removing said solvent to produce a dried mixture;

(c) hydrating said dried mixture in an aqueous buffer to produce an aqueous mixture, said aqueous buffer being essentially free of detergent;

(d) adding at least one HDL apolipoprotein to said aqueous mixture;

(e) vigorously mixing by sonication, trituration, or homogenization said HDL apolipoprotein and said aqueous mixture to form said synthetic HDL spherical particle; and (f) isolating said synthetic HDL spherical particle formed in step (e).

4. The process according to claim 3, wherein said step of isolating said carrier particles, step (f) consists essentially of exclusion chromatography.

5. The process according to claim 1, wherein, in said step of adding, step (d), said apolipoprotein comprises apo A-I or apo A-II.

6. A synthetic HDL spherical particle made by the process according to claim 1, said synthetic HDL spherical particle comprising: at least one HDL apolipoprotein, at least one amphipathic lipid, and at least one hydrophobic active agent, said hydrophobic active agent being selected from the group consisting of a hydrophobic drug, an amphipathic drug, and a lipid-soluble component, and said synthetic HDL spherical particle being generally spherical and having a diameter of from about 5 nm to about 20 nm.

7. The synthetic HDL spherical particle according to claim 6, wherein said at least one HDL apolipoprotein is selected from the group consisting of HDL apolipoprotein A-I, HDL apolipoprotein A-II, HDL apolipoprotein A4, HDL apolipoprotein C, HDL apolipoprotein D, and HDL apolipoprotein E.

8. The synthetic HDL spherical particle according to claim 7, wherein said at least one HDL apolipoprotein is HDL apolipoprotein A-I.

9. The synthetic HDL spherical particle according to claim 6, wherein said at least one amphipathic lipid is a phospholipid or a glycerolipid.

10. The synthetic HDL spherical particle according to claim 9, wherein said phospholipid is selected from the group consisting of phosphatidic acid, phosphatidylcholine, phosphatidylinositol, phosphatidylserine, phosphatidylglycerol, phosphatidylethanolamine, and sphingomyelin.

11. The synthetic HDL spherical particle according to claim 6, wherein said at least one hydrophobic active agent comprises a hydrophobic drug.

12. The synthetic HDL spherical particle according to claim 11, wherein said hydrophobic drug is selected from the group consisting of ametantrone, amphotericin B, annamycin, cyclosporin, daunorubicin, diazepam, doxorubicin, elliptinium, etoposide, ketoconazole, methotrexate, miconazole, mitoxantrone, nystatin, phenytoin and vincristine.

13. The synthetic HDL spherical particle according to claim 12, wherein said hydrophobic drug is cyclosporin.

14. The synthetic HDL spherical particle according to claim 1, comprising from about 25% to about 50% (dry wt/wt) of said apolipoprotein, from about 20% to about 50% (dry wt/wt) of said amphipathic lipid, and from about 10% to about 20% (dry wt/wt) of said hydrophobic active agent.

15. The synthetic HDL spherical particle according to claim 14, wherein the percent dry weight ratio of said apolipoprotein, said amphipathic lipid, and said hydrophobic active agent is about 38:47:15.

16. The synthetic HDL spherical particle according to claim 6, wherein said hydrophobic active agent comprises a lipid-soluble component, said lipid soluble component being selected from the group consisting of:

i) a fatty acid having from 8 to 24 carbons, said fatty acid either saturated or containing one or more unsaturated bonds;

ii) an ester of said fatty acid;

iii) mono-, di-, and tri-glycerides of said fatty acid;

iv) cholesterol, or an ester thereof;

v) an antioxidant;

vi) a steroid hormone;

vii) a hydrophobic peptide, viii) vitamin A, D, E, or K; and ix) β-carotene.

17. A composition for delivery of a hydrophobic active agent comprising:

(a) a synthetic HDL spherical particle according to claim 6; and (b) a pharmaceutically acceptable aqueous medium.

18. A method of delivering a hydrophobic active agent to a mammalian subject comprising the step of administering to said subject an effective amount of said synthetic HDL spherical particle of claim 6.

19. A method of delivering a hydrophobic active agent to a mammalian subject comprising the step of administering to said subject an effective amount of said composition of claim 17.

20. A method of reducing renal toxicity of a hydrophobic active agent comprising the step of administering an effective amount of said synthetic HDL spherical particle according to claim 6 to a subject in need thereof.

21. A method of reducing renal toxicity of a hydrophobic active agent comprising the step of administering an effective amount of said composition according to claim 17 to a subject in need thereof.

22. The synthetic HDL spherical particle according to claim 6 wherein said at least one HDL apolipoprotein comprises a human HDL apolipoprotein.

23. The synthetic HDL spherical particle according to claim 6 wherein said at least one HDL apolipoprotein is a non-human HDL apolipoprotein.

24. The synthetic HDL spherical particle according to claim 6 wherein said at least one hydrophobic active agent comprises an amphipathic drug.

25. The synthetic HDL spherical particle according to claim 6 wherein the at least one HDL apolipoprotein comprises a HDL apolipoprotein isozyme.

26. The synthetic HDL spherical particle according to claim 25 wherein the HDL apolipoprotein isozyme comprises a human HDL apolipoprotein isozyme.

27. The synthetic HDL spherical particle according to claim 6 wherein the at least one HDL apolipoprotein comprises a recombinant HDL apolipoprotein.

28. The synthetic HDL spherical particle according to claim 27 wherein the recombinant HDL apolipoprotein is a recombinant human HDL apolipoprotein.

* * * * *

UNITED STATES PATENT AND TRADEMARK OFFICE
CERTIFICATE OF CORRECTION

PATENT NO.   : 6,514,523 B1
DATED        : February 4, 2003
INVENTOR(S)  : Daniel L. Sparks Page 1 of 1

It is certified that error appears in the above-identified patent and that said Letters Patent is hereby corrected as shown below:

Column 13,
Lines 31-32, should read -- ...according to claim 6, comprising ... --.

Signed and Sealed this

Ninth Day of December, 2003

JAMES E. ROGAN
*Director of the United States Patent and Trademark Office*